United States Patent [19]
Galato

[11] Patent Number: 6,027,489
[45] Date of Patent: Feb. 22, 2000

[54] DEVICE FOR THE CONNECTION IN A STERILE ENVIRONMENT OF A PERITONEAL CATHETER TO A DIALYSIS LIQUID DRAIN OR FEED TUBE

[75] Inventor: Raffaele Galato, Segrate, Italy

[73] Assignee: Haemopharm Industry AG, Vaduz, Luxembourg

[21] Appl. No.: 08/981,053

[22] PCT Filed: Jun. 8, 1996

[86] PCT No.: PCT/EP96/02533

§ 371 Date: Dec. 11, 1997

§ 102(e) Date: Dec. 11, 1997

[87] PCT Pub. No.: WO97/00095

PCT Pub. Date: Jan. 3, 1997

[30] Foreign Application Priority Data

Jun. 16, 1995 [IT] Italy ................................. MI95A1292

[51] Int. Cl.[7] .................................................. A61M 25/00
[52] U.S. Cl. ......................... 604/533; 604/533; 604/539
[58] Field of Search .............................. 604/283, 82, 258, 604/317, 322, 905, 533, 534, 535, 536, 537, 538, 539; 128/760, 762

[56] References Cited

FOREIGN PATENT DOCUMENTS

| 0 230 864 | 8/1987 | European Pat. Off. . |
|---|---|---|
| 33 47 183 A1 | 6/1984 | Germany . |
| 96/05883 | 2/1996 | WIPO . |

*Primary Examiner*—Corrine McDermott
*Assistant Examiner*—Kent Gring
*Attorney, Agent, or Firm*—Millen, White, Zelano & Branigan

[57] ABSTRACT

A device for alternate sterile connection of a peritoneal catheter, permanently attached to a patient, to a drain tube and to a feed tube for a dialysis liquid, which apparatus comprises a shell in which a first chamber, a second chamber and a connection channel between said chambers are formed and filled with a disinfecting liquid. The chambers include respective couplings for releasable and repeatable coupling the peritoneal catheter and the drain or feed tube with the chambers in conditions of full immersion in the disinfecting liquid. This arrangement makes a tight sterile connection between said catheter and, alternately, said drain and feed tubes via said connection channel.

12 Claims, 5 Drawing Sheets

DEVICE FOR THE CONNECTION IN A STERILE ENVIRONMENT OF A PERITONEAL CATHETER TO A DIALYSIS LIQUID DRAIN OR FEED TUBE

The present invention relates to a device for the connection in a sterile environment of a peritoneal catheter to a tube for draining or feeding dialysis liquid.

Among the peritoneal dialysis techniques for the treatment of uraemic patients, continuous ambulatorial peritoneal dialysis (CAPD) is of great importance.

This technique, devised in 1975, consists in connecting a plastic container with approximately two liters of a dialysis liquid (a solution with added glucose normally isosmotic with plasma) to a peritoneal catheter permanently attached to the patient, by means of a short plastic tube with appropriate connectors at its two ends. After connection, the dialysis liquid fills the peritoneal cavity, where the blood which surrounds the peritoneal membrane exchanges the substances present in the aqueous phase and transfers the uraemic toxins to the dialysis liquid. After an appropriate space of time, the peritoneal cavity is emptied by connecting a drain tube to the peritoneal catheter.

For effective depuration of the patient, the aforementioned procedure has to be repeated daily at least four times during the day. This exposes the patient to the risk that, during the manoeuvres for permanent catheter connection to the drain tube first, in order to empty the peritoneal cavity of the liquid which is not full of toxins, and to the bag subsequently, so as to fill the peritoneal cavity with clean dialysis liquid, pathogenic agents may be introduced into the peritoneal cavity, causing the onset of bacterial peritonitis.

In view of the state of the art described, the object of the present invention is that of providing a device which enables the connection in a sterile environment of the peritoneal catheter to the drain tube first and to the feed tube for dialysis liquid subsequently, in order to reduce to a minimum the possibility during these operations of pathogenic agents being introduced into the peritoneal cavity.

In accordance with the present invention, this object is achieved thanks to a device for the connection in a sterile environment of a peritoneal catheter, permanently attached to a patient, to a drain tube or feed tube for a dialysis liquid, characterised in that it comprises a shell wherein a first chamber and a second chamber are formed, which chambers are suitable for being filled with a disinfecting liquid, and a connection channel which connects the two chambers one to the other. Respective coupling means are also provided in each chamber for coupling, in conditions of immersion in the disinfecting liquid, to said peritoneal catheter and said drain tube or said feed tube respectively, to form via said connection channel a sealed connection between said catheter and said drain tube or said feed tube.

Thanks to the device according to the present invention, the peritoneal catheter may be connected either to the drain tube or to the feed tube in a totally sterile environment, in that coupling of the peritoneal catheter, of the drain tube and of the feed tube to the coupling means provided in the chambers filled with disinfecting liquid takes place in conditions of immersion in the disinfecting liquid itself.

Preferably, said shell is also provided with an additional pair of chambers, also connected one to the other and to the chambers of the first pair in order to be also filled with said disinfecting liquid, each chamber of said second pair being suitable for holding, in conditions of immersion in the disinfecting liquid, a cap for closing said peritoneal catheter and said feed tube. In this way, the operations of removing the closure caps normally provided at the ends of the peritoneal catheter and of the feed tube may be performed in a fully sterile environment.

These and other features and advantages of the present invention will be made clearer from the following detailed description of two of its embodiments, illustrated by way of non-limiting examples in the accompanying drawings, in which.

Figure 1:
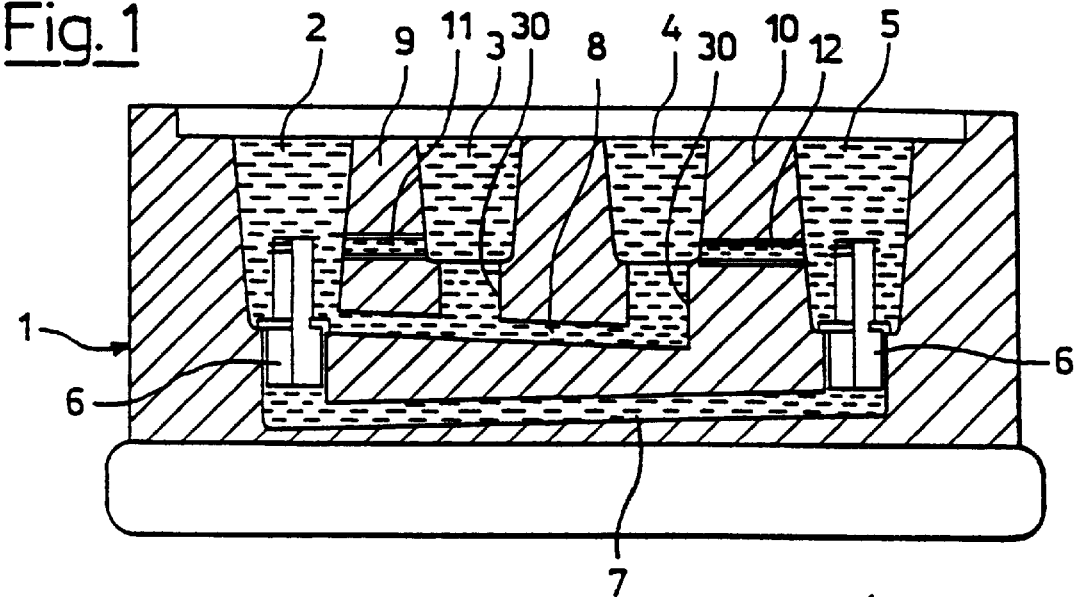
FIG. 1 is a view sectioned along a vertical plane of a device according to a first embodiment of the present invention.
Figure 2:
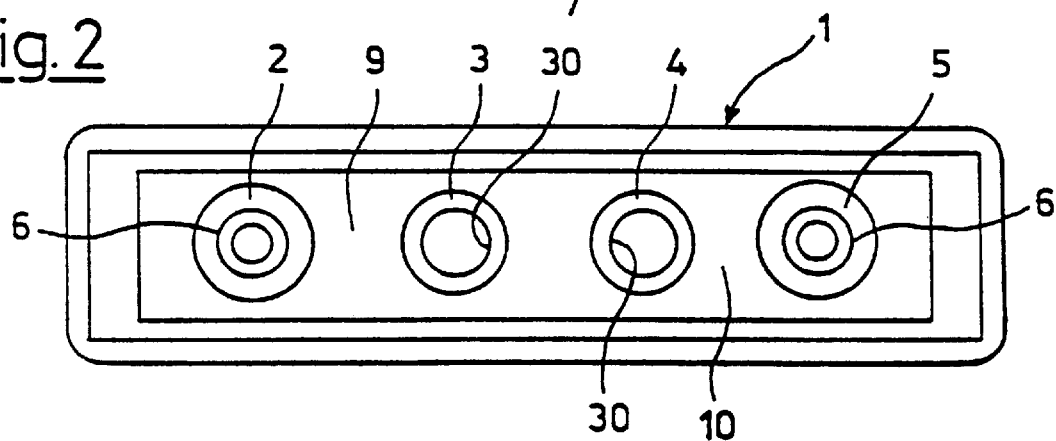
FIG. 2 is a plan view of the device of FIG. 1.

Referring to FIGS. 1 and 2, they show in a section along a vertical plane a first embodiment of a device for the connection in a sterile environment of a peritoneal catheter, permanently attached to a patient, to a tube for draining the dialysis liquid present in the peritoneal cavity of the patient, or to a tube for feeding clean dialysis liquid, normally contained in a bag.

Figure 7:
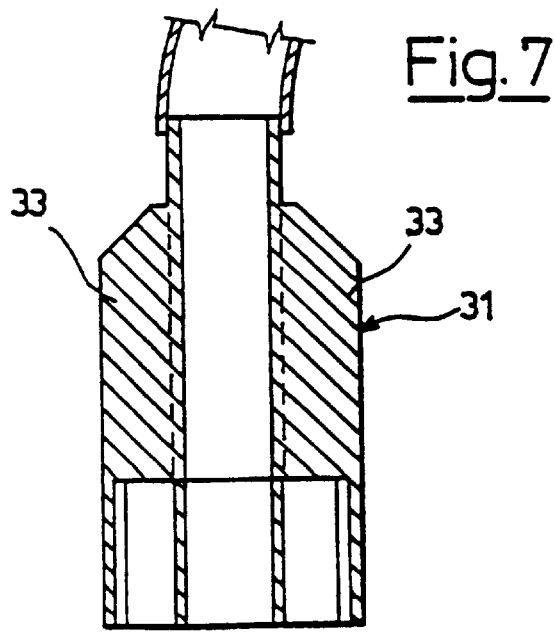
FIG. 7 is a sectioned view of a connector with which the ends of the peritoneal catheter and of a feed tube are normally provided.

The device substantially consists of a shell 1 inside whereof four chambers 2, 3, 4 and 5 are formed, substantially conical in shape. On the base of the chambers 2 and 5 two connectors 6 are stably housed, each provided with a central through hole, complementary to connectors 31 (of the so-called "luer-lok" type shown in FIG. 7) normally provided at the ends of the peritoneal catheter and of the tube for feeding dialysis liquid. In the example shown, since it is assumed that the connectors 31 placed at the ends of the catheter and of the feed tube are male connectors, the connectors 6 provided on the base of the chambers 2 and 5 are female connectors, with tubular appendage and external threading. However, should the connectors at the ends of the catheter and of the feed tube be female connectors, the connectors 6 provided on the base of the chambers 2 and 5 should be male connectors.

On the base of the shell 1, a connection channel 7 connects the chambers 2 and 5 via the through holes of the connectors 6.

The central chambers 3 and 4, which in this first embodiment have a smaller depth than the chambers 2 and 5, lead on the base to a second connection channel 8 which also flows into the chamber 2 near the base of the latter. Moreover, in the baffle 9 which separates the chambers 2 and 3 and in the baffle 10 which separates the chambers 4 and 5 two further connection channels 11 and 12 are formed which connect the chambers 2 and 3 and the chambers 4 and 5 respectively.

All the chambers are however connected one to the other.

Figure 8:
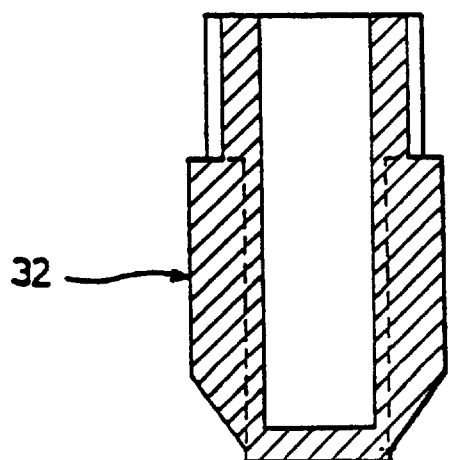
FIG. 8 is a sectioned view of a cap suitable for being coupled to the connector of FIG. 7 to close said peritoneal catheter and said feed tube.

The two central chambers 3 and 4 are also provided, near their base, with respective seats 30 suitable for holding closure caps 32 (of the type shown in FIG. 8) which can be screwed onto the connectors 31 provided at the ends of the peritoneal catheter and of the feed tube to close the latter tight.

For the use of the device described above, it is first of all necessary to fill the chambers with a disinfecting liquid, typically 100% "Amuchina" or the like. Since the four chambers 2–5 are all connected one to the other, any chamber can be chosen in which to pour the disinfectant. Filling proceeds until the level of disinfectant reached a reference notch. This starting conditions is illustrated in FIG. 1; however chambers 2–5, as also all the connection channels 7, 8, 11 and 12, are filled with the disinfecting liquid.

In the following description it will be assumed that use is made of a peritoneal dialysis device of the type described in a contemporary Italian patent application in the name of the same applicant, a device which comprises a bag 12 (FIGS. 3–6) containing the dialysis liquid and from which two flexible tubes 13 and 14 extend and which are connected to a portion 15 of the same bag 12 which can be separated hydraulically, for example by means of a clip 16, from the remaining of the bag 12. This dialysis device, which constituted an improvement of the known connection system referred to as "Y-set", is merely mentioned here by way of an example, in that the connection device of the present invention can also be used with other devices, for example the Y-set.

Figure 3:
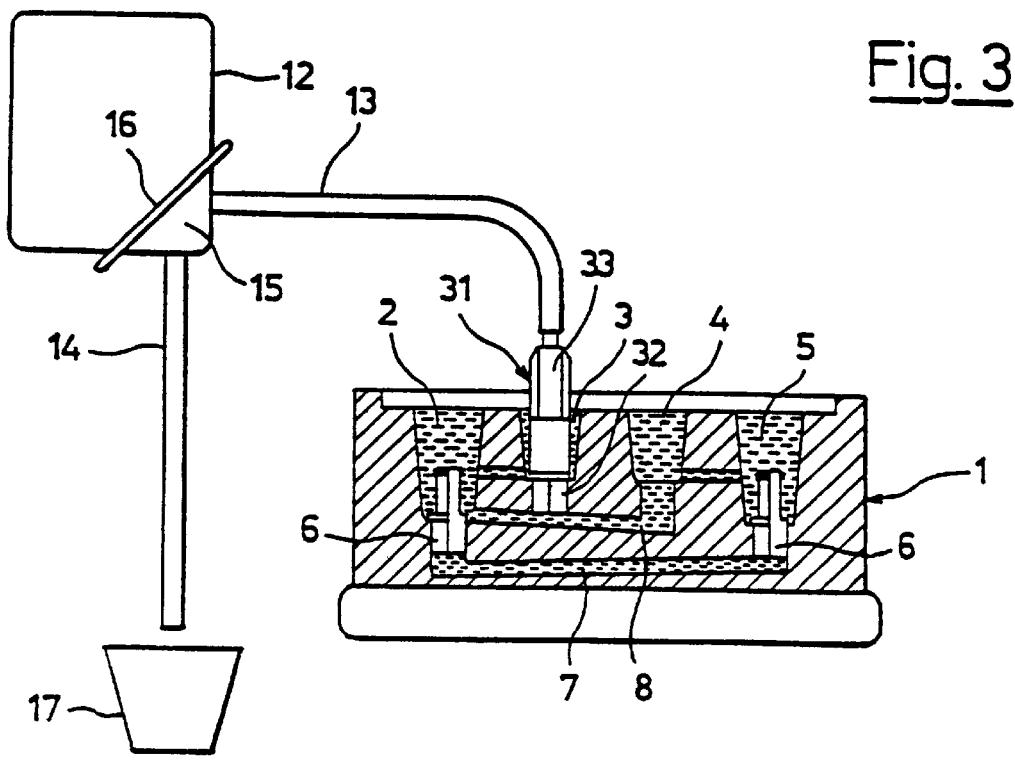
FIGS 3–6 show four phases of an operation of connecting a peritoneal catheter to a bag containing a dialysis liquid.

The first operation which the patient has to perform consists of draining the dialysis liquid present in the peritoneal cavity. For this purpose the bag portion 15 is isolated hydraulically from the remaining of the bag 12 by means of the clip 16, one (no. 14) of the two tubes which extend from the bag 12, after the respective closure cap 32 has been removed therefrom, is connected to a drain recipient 17, and the end of the other tube 13, still provided with the respective closure cap 32, is inserted by a downward movement in the chamber 3 (an operation facilitated by the conical shape of the chambers, which avoids problems of alignment) so that the cap 32 engages in the seat 30 (FIG. 3).

Figure 4:
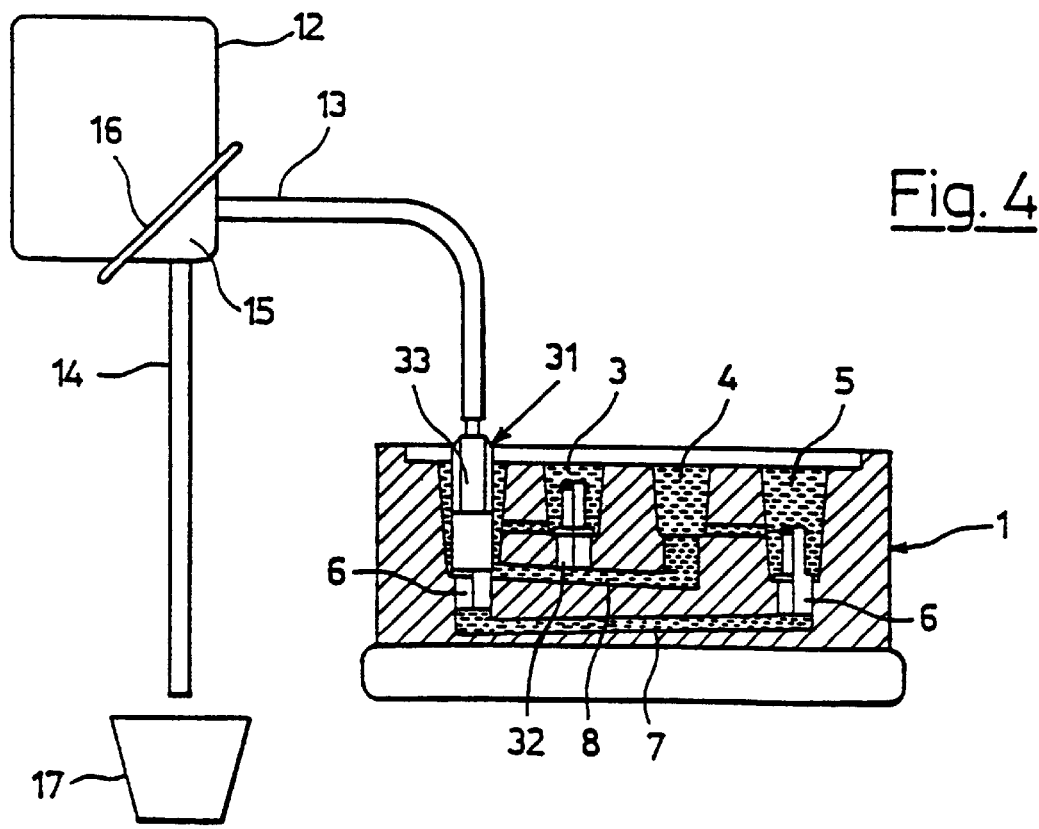

By acting on a handle 33 of the male connector 31 (FIG. 7) placed at the end of the tube 13, the patient makes it rotate by approximately half a turn in relations to the cap 32, which is maintained fixed in its seat 30, until the connector 31 is unscrewed from the cap 31. Then the connector 31 is inserted in the chamber 2 and is screwed onto the female connector 6 housed on the base of the latter (FIG. 4). It should be noted that the operations of unscrewing the cap 32 and screwing of the male connector 31 on the female connector 6 occur in conditions of immersion in the disinfecting liquid, and hence in a sterile environment, without the need for the patient to touch the open end of the connector 31 or to put the latter down in order to perform other operations. Neither is it necessary for the patient to wet his or her fingers with disinfectant, in that the handle 33 is sufficiently extended to project in relation to the surface of the disinfecting liquid. Once the connection has been made, both the cap 32 and the connector 31 remain immersed in the disinfecting liquid.

Thus the device 1 is connected to a drain conduit, consisting of the tube 13, the bag portion 15 isolated from the remaining of the bag 12 and the tube 14.

Figure 5:
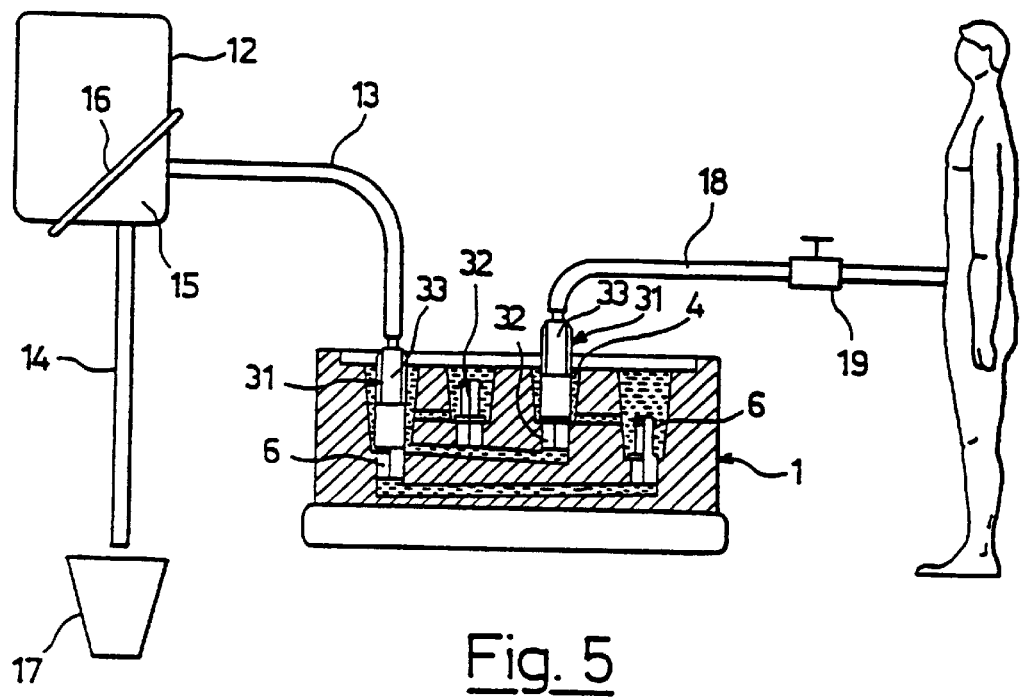

At this point the patient must connect his or her peritoneal catheter to the device 1. This is carried out in a wholly similar manner to what has been described: the patient inserts the end of the catheter 18 (FIG. 5), still provided with the respective closure cap 32, in the chamber 4, so that the cap 32 is engaged in the respective seat 30 (FIG. 5).

Figure 6:
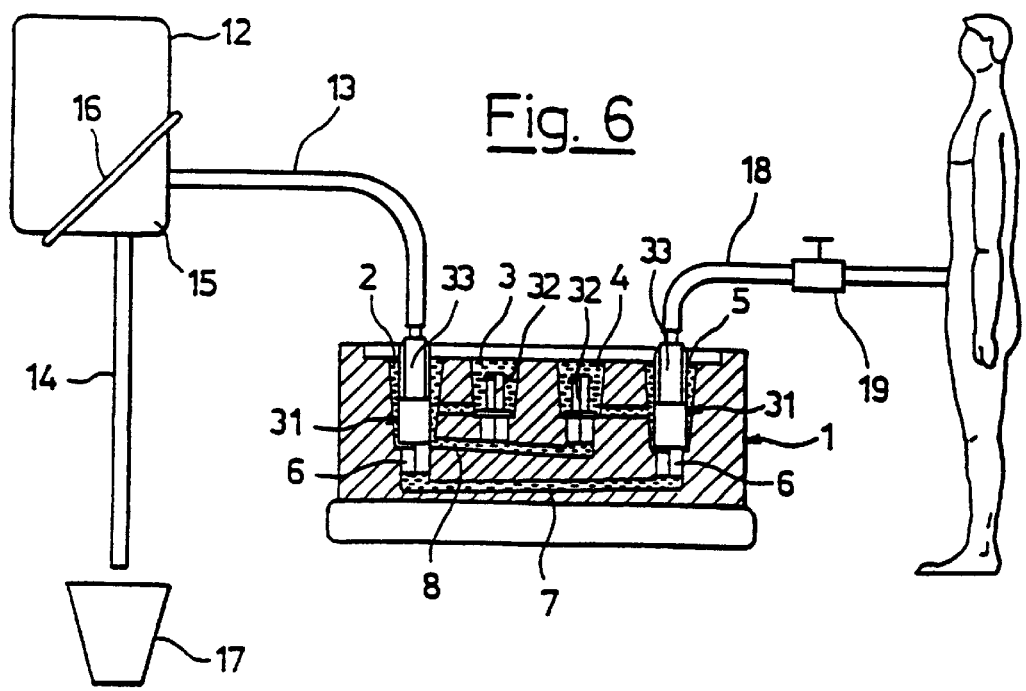
Figure 9:
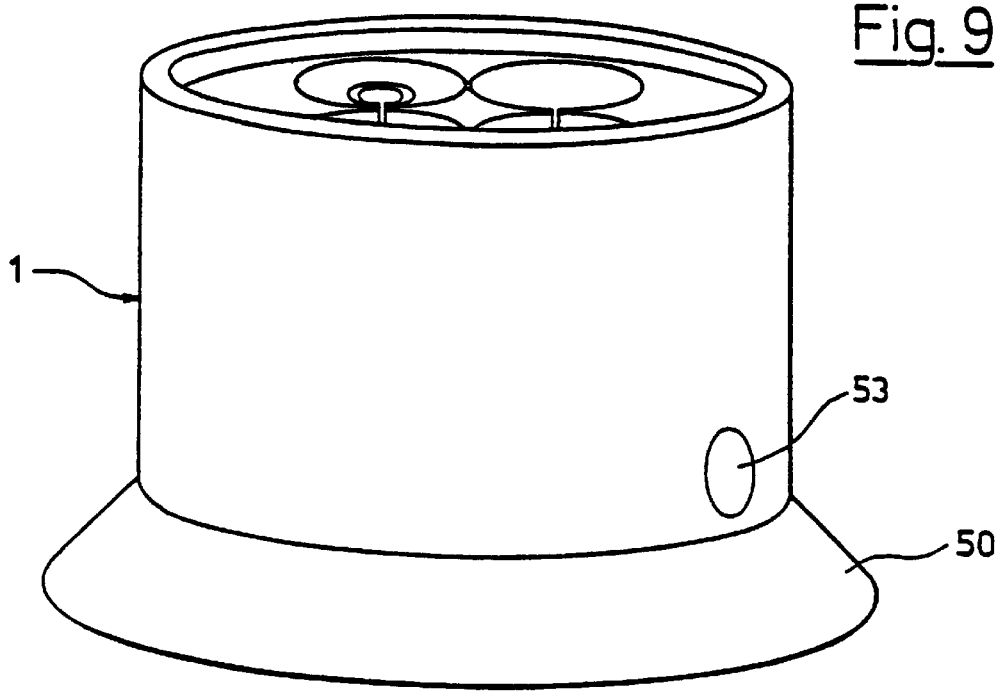
FIG. 9 is a perspective view of a device according to a second embodiment of the present invention.
Figure 10:
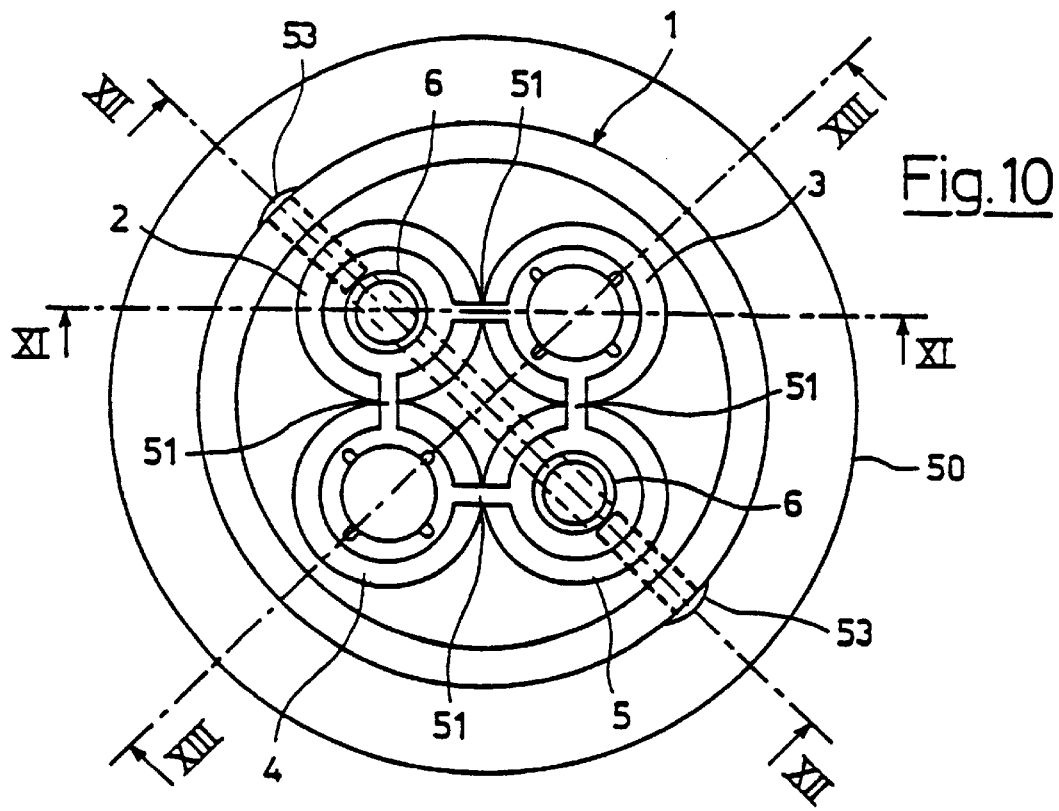
FIG. 10 is a plan view of the device of FIG. 9.
Figure 11:
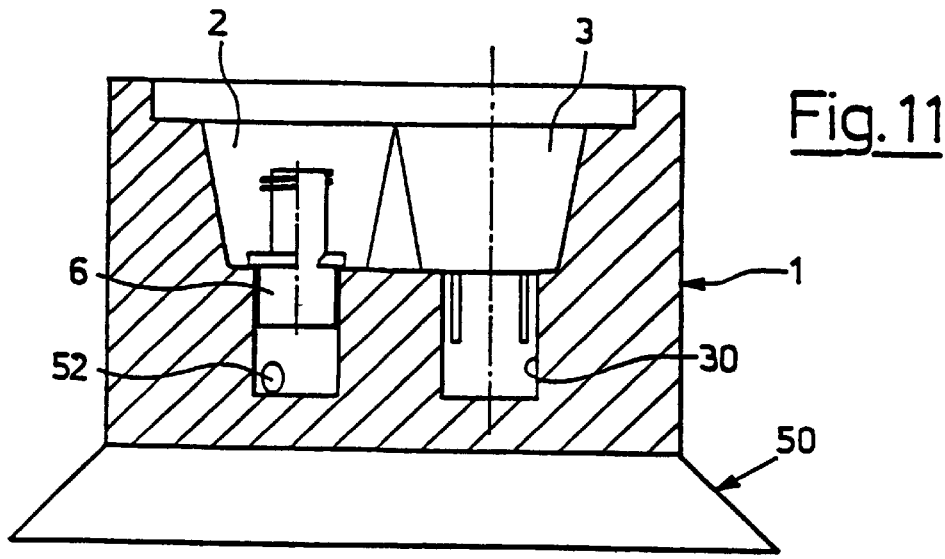
FIG. 11 is a section along line XI—XI of FIG. 10.
Figure 12:
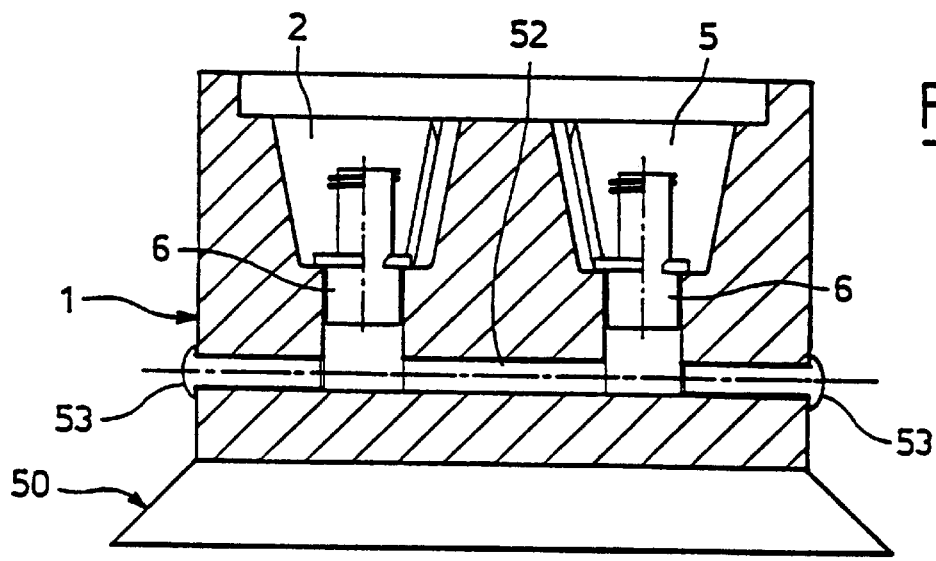
FIG. 12 is a section along line XII—XII of FIG. 10.
Figure 13:
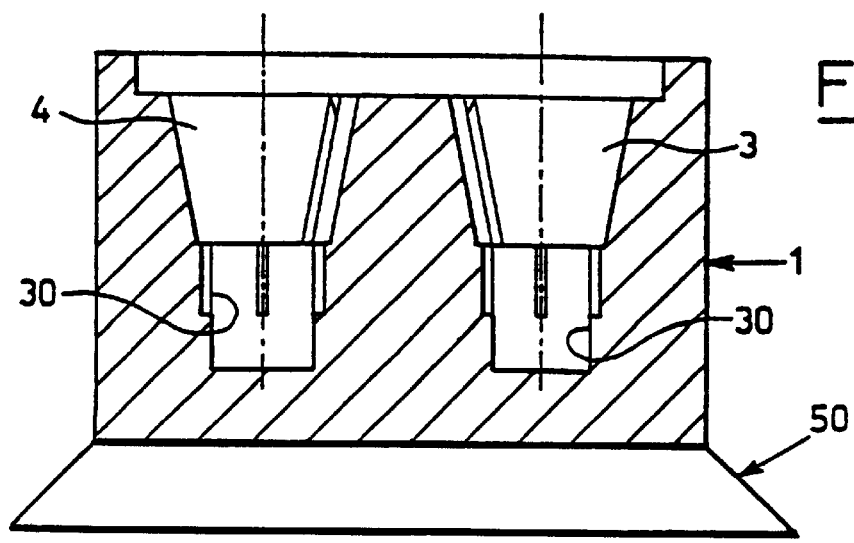
FIG. 13 is a section along line XIII—XIII of FIG. 10.

By acting on the handle 33 of the male connector 31, the patient unscrews the latter from the cap 32 (maintained fixed in the seat 30), then inserts the connector 31 in the chamber 5 and screws it onto the female connector 6 provided on the base of the latter (FIG. 6).

In this way the catheter 18 is connected to the tube 13 via the connection channel 7.

By opening a tap 19 normally provided on the catheter 18 (typically consisting of a so-called "roller"), the operation of draining the dialysis liquid present in the peritoneal cavity of the patient begins. During this operation, the dialysis liquid to be drained empties the connection channel 7 of the disinfecting liquid.

After the draining phase, the tube 14 of the bag 12 is closed near its end connected to the bag itself, for example by means of another clip, and the bag portion 15 is reconnected to the remaining of the bag 12 (which contains the dialysis liquid) by removing the clip 16. The dialysis liquid present in the bag 12 is thus fed, via the tube 13, the channel 7 and the catheter 18, to the peritoneal cavity of the patient.

At the end of the feed phase, the patient closes the tap 19, unscrews the connector 31 of the catheter 18 from the connector 6 on the base of the chamber 5, removes it from the chamber 5, inserts it in the chamber 4, screwing it on the relevant closure cap 32, and finally removes the connector 31, with the relevant cap 32, from the chamber 4. Then, in a wholly similar manner, the patient disconnects the connector 31 of the tube 13 from the connector 6 on the base of the chamber 2, inserts it in the chamber 3, screwing it on the relevant closure cap 32, and removes everything from the chamber 3.

FIGS. 9–13 show a second embodiment of the connection device according to the present invention.

In this embodiment, the shell 1 of the connection device has a substantially cylindrical shape, with a widened base 50. The four chambers 2, 3, 4 and 5 are arranged in a circumferential series in the shell 1 and all have the same depth. The chambers are connected two by two thanks to connection channels 51. Moreover, the chambers 2 and 5 are connected at their base thanks to a connection channel 52 diametrical to the shell 1 and open at its two ends to facilitate the operation of emptying and washing of the connection device at the end of the dialysis operations. Two plugs 53 are also provided for closing the openings of the connection channel 52 during the dialysis operations.

As indicated by the foregoing description, the connection device of the present invention, involving operations which are performed in sequence and not simultaneously, requires the use of only one hand.

Another advantage of the device of the present invention lies in the fact that it can be reused for a theoretically infinite number of exchanges of dialysis liquid. It thus avoids the use of expensive safety devices related to the bag assembly, which after use are thrown away together with the latter.

I claim:

1. A device for alternate sterile connection of a drain tube and feed tube to one end of a peritoneal catheter which catheter is adapted to be permanently attached to a patient at the other end for treating the patient with dialysis liquid, the device comprising:

a shell in which a first chamber, a second chamber and a connection channel between said chambers are formed and filled with a disinfecting liquid, wherein said chambers include respective couplings for releasable and repeatable alternative coupling of said peritoneal catheter to said drain tube and to said feed tube with said chambers in conditions of full immersion of the couplings in the disinfecting liquid whereby a tight sterile connection between said catheter and, alternately, said drain and feed tubes occurs during treatment of the patient so that the device is reusable for successive feeding and draining procedures.

2. A device according to claim 1 wherein the couplings selectively open and close connections between the peritoneal catheter and the drain tube and the peritoneal catheter and feed tube via operators which are outside of the disinfecting liquid.

3. A device according to claim 2 wherein the operators are handle portions of the couplings which extend out of the disinfecting liquid.

4. A device according to claim 1, wherein the chambers each have a base or wherein the connection channel is connected to the bases of the two chambers.

5. A device according to claim 4, wherein said connection channel opens outside of the device at an open end, the end being provided with a removable plug for closing the open end of the connection channel.

6. A device according to claim 5, which further includes a third chamber and a fourth chamber connected one to the other and to said first and second chambers so as to be filled by said disinfecting liquid, said third and fourth chambers each comprising a respective seat suitable for housing, in conditions of immersion in the disinfectant, a closure cap which can be coupled to said complementary connector normally provided at the end of the catheter and of the feed tube to close the catheter and feed tube tight.

7. A device according to claim 6, wherein said first, second, third and fourth chambers are arranged in a circumferential series and are connected one to the other and two by two via respective connection channels.

8. A device according to claim 4, wherein said couplings each comprise an internally hollow connector which can be coupled to a complementary connector provided at the end of said peritoneal catheter and of said feed and drain tubes.

9. A device according to claim 8, wherein the connectors provided in the first and second chambers are both female connectors which can be coupled to male connectors provided at the end of said peritoneal catheter and of said feed and drain tubes.

10. A device according to claim 8, wherein the connectors provided in the first and second chamber are both male connectors which can be coupled to female connectors provided at the end of said peritoneal catheter and of said feed and drain tubes.

11. A device according to claim 10, wherein said third and fourth chambers are connected from bases thereof to a second connection channel which in turn is connected to one of said first and second chambers.

12. A device according to claim 11, wherein each of said third and fourth chambers leads into a respective one of said first and second chambers via a respective connection channel formed in a respective baffle.

* * * * *